(12) United States Patent
Bernat et al.

(10) Patent No.: US 8,460,897 B1
(45) Date of Patent: Jun. 11, 2013

(54) METHODS OF CULTURING FUNGI AND PRODUCING CELLULASES AND CHITIN

(75) Inventors: Eugene N. Bernat, Upton, MA (US); David Scott Hibbett, Upton, MA (US); Dimitrios Floudas, Worcester, MA (US)

(73) Assignee: Eclipse Bioproducts, LLC, Holyoke, MA (US)

( * ) Notice: Subject to any disclaimer, the term of this patent is extended or adjusted under 35 U.S.C. 154(b) by 305 days.

(21) Appl. No.: 12/969,614

(22) Filed: Dec. 16, 2010

Related U.S. Application Data

(60) Provisional application No. 61/287,329, filed on Dec. 17, 2009.

(51) Int. Cl.
| | | |
|---|---|---|
| C12P 21/02 | (2006.01) | |
| C12P 9/28 | (2012.01) | |
| C12N 9/26 | (2006.01) | |
| C12N 1/14 | (2006.01) | |
| C07D 309/14 | (2006.01) | |
| C08L 1/02 | (2006.01) | |

(52) U.S. Cl.
USPC ......... 435/71.1; 435/85; 435/203; 435/256.8; 536/20; 524/35

(58) Field of Classification Search
USPC ...... 435/71.1, 85, 203, 256.8; 536/20; 524/35
See application file for complete search history.

(56) References Cited

U.S. PATENT DOCUMENTS

| | | | |
|---|---|---|---|
| 3,858,492 A | 1/1975 | Makai et al. | |
| 4,144,354 A | 3/1979 | Unno et al. | |
| 4,333,955 A | 6/1982 | Murata et al. | |
| 5,464,766 A | 11/1995 | Bruno | |
| 5,786,188 A | 7/1998 | Lamar et al. | |
| 5,905,035 A | 5/1999 | Okada et al. | |
| 6,197,573 B1 | 3/2001 | Suryanarayan et al. | |
| 6,255,085 B1 | 7/2001 | Chen et al. | |
| 6,399,338 B1 | 6/2002 | Chen et al. | |
| 6,485,946 B1 | 11/2002 | Chen et al. | |
| 6,664,095 B1 | 12/2003 | Suryanarayan et al. | |
| 6,693,188 B2 | 2/2004 | Bohlmann et al. | |
| 2005/0032206 A1 | 2/2005 | Hasegawa et al. | |
| 2005/0059142 A1 | 3/2005 | Vinarov et al. | |
| 2005/0176583 A1 | 8/2005 | Stamets | |
| 2006/0277632 A1 | 12/2006 | Carr et al. | |
| 2007/0122869 A1 | 5/2007 | Hasegawa et al. | |
| 2007/0172938 A1 | 7/2007 | DeGuchi et al. | |

(Continued)

FOREIGN PATENT DOCUMENTS

WO 0029544 A1 5/2000

OTHER PUBLICATIONS

Novotný et al., "*Irpex lacteus*, a white rot fungus applicable to water and soil bioremediation," Appl Microbiol Biotechnol 54:850-853, 2000.*

(Continued)

*Primary Examiner* — Rosanne Kosson
(74) *Attorney, Agent, or Firm* — Cantor Colburn LLP

(57) ABSTRACT

The fungus *Irpex lacteus* is efficiently cultured on a solid substrate with a high content of crystalline cellulose. The fungal culture can be used to produce cellulases that are useful in conversion of cellulose to sugars. The fungal culture can also be used to produce chitin, which is itself valuable and can also be converted to chitosan. Use of the fungal culture for co-production of cellulases and chitin is also described.

18 Claims, 1 Drawing Sheet

U.S. PATENT DOCUMENTS

| | | | |
|---|---|---|---|
| 2007/0207108 | A1 | 9/2007 | Yamasaki et al. |
| 2008/0005046 | A1 | 1/2008 | Staments |
| 2008/0046277 | A1 | 2/2008 | Staments |
| 2008/0264858 | A1 | 10/2008 | Staments |

OTHER PUBLICATIONS

Mamma et al., "Adsorption of major endoglucanase from *Thermoascus aurantiacus* on cellulosic substrates," World J Microbiol Biotechnol 25:781-788, Jan. 2009.*

Adney et al., "measurement of Cellulase Cactivities", National REnewable Energy Laboratory, Aug. 12, 1996, available at http://www.nrel.gov/biomass/pdfs/42628.pdf (last visted Nov. 2, 1999).

Cen et al., "Production of Cellulase by Solid-State Fermentation", Advances in Biochemical Engineering/Biotechnology, 1999, vol. 65, p. 69-92.

Da Silva Amorim et al., "Faster chitosan production by mucoralean strains in submerged culture," Brazilian Journal of Microbiology, 2001, vol. 32, p. 20-23.

Dimario et al. "Chitin and Chitosan from Basidiomycetes", International Journal of Biological Macromolecules, 2008, vol. 43, No. 8, pp. 8-12.

Fang et al., "Submerged fermentation of higher fungus *Ganoderma lucidum* fro production of valuable bioactive metabolites—ganoderic acid and polysaccharide", Biochemical Engineering Journal, 2002, vol. 10, p. 61-65.

Gupte et al., "Ligninolytic enzyme production under solid-state fermentation by white rot fungi", Journal of Scientific and Industrial Research, 2007, vol. 66, No. 8, p. 611-614.

Hankin et al. "Solid Media Containing Carboxymethylcellulose to Detect Cx Cellulase Activity of Micro-organisms", Journal of General Microbiology, 1977, vol. 98, p. 109-115.

Holker et al., "Biotechnological advantages of laboratory-scale solid-state fermentation with fungi", Applied Microbiology & Biotechnology, 2004, vol. 64, p. 175-186.

Jecu, "Solid state fermentation of agricultural wastes for endoglucanase production", Industrial Crops and Products, 2000, 11, p. 1-5.

Kachlishvili et al. "Effect of nitrogen source on lignocellulolytic enzyme production by white-rot basidiomycetes under solid-state cultivation", World Journal of Microbiology & Biotechnology, 2005, vol. 22, p. 391-397.

Lenz et al. "Trickle-film Processing: An Alternative for Producing Fungal Enzymes", BIOForum Europe, Jun. 2004, p. 55-57, GIT Verlag GmbH & Co. KG, Darmstadt.

Liming et al., "High-yield cellulase production by *Trichoderma reesei* ZU-02 on corn cob residue", Bioresource Technology, 2004, vol. 91, p. 259-262.

Liu, "Co-production of lactic acid and chitin using a pelletized filamentous *Rhizopus oryzae* culture from cull potatoes", 2005, Ph.D Thesis, Washington State University.

Montenegro et al., "Growth of *Cunninghamella elegans* UCT 542 and production of chitin and chitosan using yam bean medium", Electronic Journal of Biotechnology, 2007, vol. 10, No. 1, p. 61-68.

Ng, "Peptides and proteins from fungi", Peptides, 2004, vol. 25, No. 6, p. 1055-1073.

Nwe et al. "Effect of urea on fungal chitosan production in solid substrate fermentation", Process Biochemistry, 2004, vol. 39, p. 1639-1642.

Pandey et al., "Solid state fermentation of the production of industrial enzymes", Current Science, 1999, volumne 77, No. 1, pp. 149-162.

Pochanavanich et al., "Fungal chitosan production and its characterization", Letters in Applied Microbiology, 2002, vol. 35, p. 17-21.

Rajarathnam et al., "Biodegradative and biosynthetic capacities of mushrooms: present and future strategies", Critical Reviews in Biotechnology, 1998, vol. 18, p. 91-236.

Rodriguez Couto et al., "Application of solid-state fermentation to ligninolytic enzyme production", Biochemical Engineering Journal, 2005, vol. 22, p. 211-219.

Rahardjo, "Fungal Mats in Solid-State Fermentation", 2005, Ph.D Thesis, Wageningen University, Apr. 18, 2005.

Royer et al., "Production of mycelial protein and hydrolytic enzymes from paper mill sludges by cellulolytic fungi", Journal of Industrial Microbiology and Biotechnology, 1987, vol. 2, No. 1, p. 9-13.

Shanmugam et al., "Biological Decolourization of Textile and Paper Effluents by *Pleurotus florida* and *Agaricus bisporus* (White-rot Basidiomyctes)", World Journal of Microbiology and Biotechnology, 2005, vol. 21, No. 6-7, p. 1149-1151.

Singhania et al., "Improved Cellulase Production by *Trichoderma reesei* RUT C30 under SSF Through Process Optimization", Applied Biochemistry and Biotechnology, 2007, vol. 142, p. 60-70.

Tao et al., "A Novel Design of Solid State Fermenter and Its Evaluation for Cellulase Production by *Trichoderma veride* SL-1", Biotechnology Techniques, 1997, vol. 10, p. 889-894.

Tsao et al., "Repeated Solid-Phase Fermentation and Extraction from Enzyme Production", Applied Biochemistry and Biotechnology, 2000, vol. 84-86, pp. 505-524.

Villena et al. "Production of cellulase by *Aspergillus niger* biofilms developed on polyester cloth", Letters in Applied Microbiology, 2006, vol. 43, p. 262-268.

Wu et al., "Chitin and Chitosan—Value Added Products from Mushroom Waste", J. Agic. Food Chem., 2004, vol. 52, p. 7905-7910.

\* cited by examiner

METHODS OF CULTURING FUNGI AND PRODUCING CELLULASES AND CHITIN

CROSS REFERENCE TO RELATED APPLICATION

This application claims the benefit of U.S. Provisional Patent Application Ser. No. 61/287,329, filed Dec. 17, 2009, which is fully incorporated herein by reference.

BACKGROUND OF THE INVENTION

Fungi are critical organisms in the recycling of organic matter in nature. Fungi hydrolyze their organic surrounding habitat by producing extra cellular enzymes that they excrete into their surroundings. The enzymes produced by fungi are specific to the species of fungi and the substrate (food source) on which they grow. The environmental conditions present, i.e., the food sources available to the organism, induce the production of the specific enzymes required to catalyze the release of soluble nutrients from the organic matter in the organism's surroundings which can then be absorbed through the fungal cell walls and used by the organism for biosynthesis.

There are estimated to be over 1.5 million species of fungi with approximately 100,000 having been identified. The primary industrial use of fungi is the production of enzymes and fermented foods. Two species in particular are industrial workhorses: *Trichoderma reesei* and *Aspergillus niger*. However, literally thousands of fungi occupy the same ecological niche as *Trichoderma* and *Aspergillus* as decomposers and recyclers of cellulosic biomass and as yet have not been exploited commercially. The use of these organisms has co-developed with industrial fermentation technologies relying on submerged fermentation reactors and simplified liquid culture media. In most cases these organisms have been genetically manipulated to grow under liquid fermentation conditions and have been engineered to synthesize specific enzymes when stimulated by specific soluble inducing agents. However, the vast majority of fungi are aerobic organisms that cannot survive in an anaerobic condition or thrive in an aerobic submerged condition and whose enzyme expression is triggered by exposure to a natural, complex solid biologic substrates as a food source.

Solid state fermentation of fungi is known. See, for example, A. Pandey, P. Selvakumar, C. R. Soccol, P. Nigam, "Solid state fermentation of the production of industrial enzymes", *Current Science*, 1999, volume 77, no. 1, pages 149-162; and P. Cen, L. Xia, "Production of Cellulase by Solid-State Fermentation", *Advances in Biochemical Engineering/Biotechnology*, 1999, volume 65, pages 69-92. However, there remains a need for improved methods and diverse organisms for culturing fungi on cellulosic solid supports to produce highly effective enzymes for use in the hydrolysis of diverse plant based lignocellulose. The need is particularly great for cellulosic supports rich in crystalline cellulose, which is difficult for *Trichoderma* and *Aspergillus* to degrade.

BRIEF DESCRIPTION OF THE INVENTION

One embodiment is a method of culturing fungi, comprising: forming a solid substrate comprising about 80 to about 98 weight percent cellulose on a dry weight basis; wherein the cellulose is about 55 to about 80 weight percent crystalline; inoculating the solid substrate with an inoculum comprising *Irpex lacteus*; and maintaining the inoculated solid substrate at a temperature of about 20 to about 40° C. and a pH of about 3 to about 7 for a time sufficient to effect colonization of the solid substrate by an *Irpex lacteus* fungal mass.

Another embodiment is a method of producing a fungal cellulase, comprising: forming a solid substrate comprising about 80 to about 98 weight percent cellulose on a dry weight basis; wherein the cellulose is about 55 to about 80 weight percent crystalline; inoculating the solid substrate with an inoculum comprising *Irpex lacteus*; maintaining the inoculated solid substrate at a temperature of about 20 to about 40° C. and a pH of about 3 to about 7 for a time sufficient to effect colonization of the solid substrate by an *Irpex lacteus* fungal mass; and extracting a cellulase from the colonized solid substrate.

Another embodiment is a method of producing fungal chitin, comprising: forming a solid substrate comprising about 80 to about 98 weight percent cellulose on a dry weight basis; wherein the cellulose is about 55 to about 80 weight percent crystalline; inoculating the solid substrate with an inoculum comprising *Irpex lacteus*; maintaining the inoculated solid substrate at a temperature of about 20 to about 40° C. and a pH of about 3 to about 7 for a time sufficient to effect colonization of the solid substrate by an *Irpex lacteus* fungal mass; and isolating chitin from the *Irpex lacteus* fungal mass.

Another embodiment is a method of co-producing a fungal cellulase and fungal chitin, comprising: forming a solid substrate comprising about 80 to about 98 weight percent cellulose on a dry weight basis; wherein the cellulose is about 55 to about 80 weight percent crystalline; inoculating the solid substrate with an inoculum comprising *Irpex lacteus*; maintaining the inoculated solid substrate at a temperature of about 20 to about 40° C. and a pH of about 3 to about 8 for a time sufficient to effect colonization of the solid substrate by an *Irpex lacteus* fungal mass; extracting a cellulase from the colonized solid substrate; and isolating chitin from the *Irpex lacteus* fungal mass.

These and other embodiments are described in detail below.

DETAILED DESCRIPTION OF THE INVENTION

Figure 1:
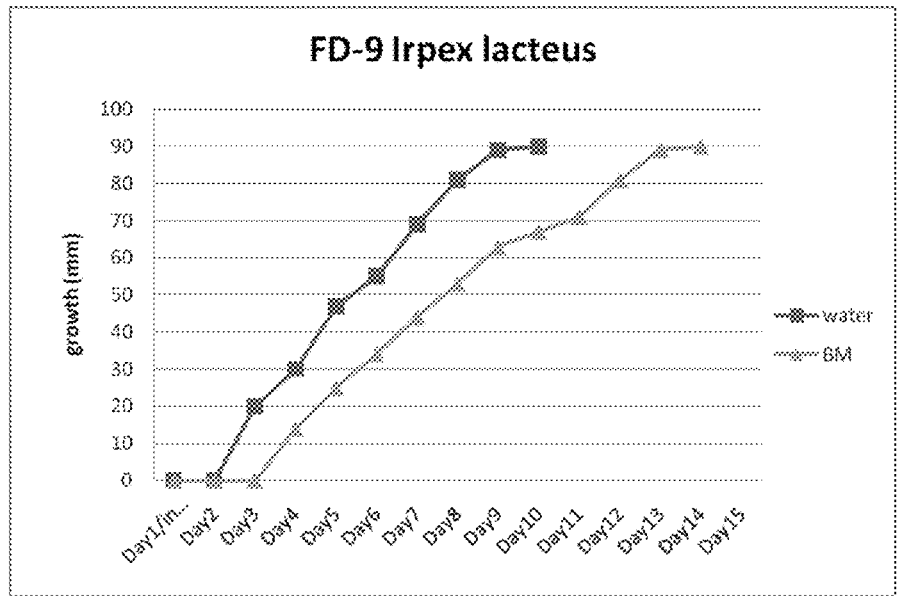
FIG. 1 is a plot of culture diameter versus time for solid substrates prepared with water (Example 1) and basal medium (Example 3).

The present invention is based, in part, on the discovery that *Irpex lacteus* is particularly adept at degrading crystalline cellulose. This interaction can be exploited in a number of different ways, including the culturing of *Irpex lacteus*, the use of *Irpex lacteus* to produce cellulase, the use of *Irpex lacteus* to produce chitin and its derivatives, and the use of *Irpex lacteus* for the co-production of cellulase and chitin. Thus, one embodiment is a method of culturing fungi, comprising: forming a solid substrate comprising about 80 to about 98 weight percent cellulose on a dry weight basis; wherein the cellulose is about 55 to about 80 weight percent crystalline; inoculating the solid substrate with an inoculum comprising *Irpex lacteus*; and maintaining the inoculated solid substrate at a temperature of about 20 to about 40° C.

and a pH of about 3 to about 7 for a time sufficient to effect colonization of the solid substrate by an *Irpex lacteus* fungal mass.

Another embodiment is a method of producing a fungal cellulase, comprising: forming a solid substrate comprising about 80 to about 98 weight percent cellulose on a dry weight basis; wherein the cellulose is about 55 to about 80 weight percent crystalline; inoculating the solid substrate with an inoculum comprising *Irpex lacteus*; maintaining the inoculated solid substrate at a temperature of about 20 to about 40° C. and a pH of about 3 to about 7 for a time sufficient to effect colonization of the solid substrate by an *Irpex lacteus* fungal mass; and extracting a cellulase from the colonized solid substrate.

Another embodiment is a method of producing fungal chitin, comprising: forming a solid substrate comprising about 80 to about 98 weight percent cellulose on a dry weight basis; wherein the cellulose is about 55 to about 80 weight percent crystalline; inoculating the solid substrate with an inoculum comprising *Irpex lacteus*; maintaining the inoculated solid substrate at a temperature of about 20 to about 40° C. and a pH of about 3 to about 7 for a time sufficient to effect colonization of the solid substrate by an *Irpex lacteus* fungal mass; and isolating chitin from the *Irpex lacteus* fungal mass.

Another embodiment is a method of co-producing a fungal cellulase and fungal chitin, comprising: forming a solid substrate comprising about 80 to about 98 weight percent cellulose on a dry weight basis; wherein the cellulose is about 55 to about 80 weight percent crystalline; inoculating the solid substrate with an inoculum comprising *Irpex lacteus*; maintaining the inoculated solid substrate at a temperature of about 20 to about 40° C. and a pH of about 3 to about 7 for a time sufficient to effect colonization of the solid substrate by an *Irpex lacteus* fungal mass; extracting a cellulase from the colonized solid substrate; and isolating chitin from the *Irpex lacteus* fungal mass.

Each of these embodiments includes the step of forming a solid substrate comprising about 80 to about 98 weight percent cellulose on a dry weight basis. Within this range, the cellulose content can be about 85 to about 95 weight percent. The cellulose is highly crystalline. Specifically, the cellulose is about 55 to about 80 weight percent crystalline, specifically about 60 to about 75 weight percent crystalline. In some embodiments, the solid substrate comprises a crystalline cellulose amount of about 44 to about 78 weight percent, specifically about 50 to about 75 weight percent, on a dry weight basis. In some embodiments, the cellulose comprises an alpha cellulose content of at least 80%, specifically at least 90%, more specifically at least 95%, based on the total weight of cellulose. In some embodiments, the cellulose is alpha cellulose. The solids components of the solid substrate can be in the form of relatively fine fibers. For example, the solid substrate can comprise, on a dry weight basis, less than 5 weight percent of fibers having a thickness greater than or equal to 500 micrometers. In some embodiments, the solid substrate can comprise, on a dry weight basis, less than 5 weight percent of fibers having a length greater than or equal to 5 millimeters.

The solid substrate can contain include substantial nitrogen content, independent of nitrogen supplements. For example, the solid substrate can have a total nitrogen content of about 1,000 to about 10,000 milligrams per kilogram on a dry weight basis. Within this range, the total nitrogen content can be about 2,000 to about 9,000 milligrams per kilogram, specifically about 3,000 to about 8,000 milligrams per kilogram, more specifically about 4,000 to about 7,500 milligrams per kilogram. Part of the total nitrogen content can be present as ammonia. Thus, the solid substrate can have an ammonia content of about 100 to about 1,000 milligrams per kilogram on a dry weight basis. Within this range, the ammonia content can be about 200 to about 750 milligrams per kilogram, specifically about 300 to about 600 milligrams per kilogram.

The solid substrate can also include substantial phosphorus content independent of phosphorus supplements. Thus, the solid substrate can have a phosphorus content of about 200 to about 2000 milligrams per kilogram on a dry weight basis. Within this range, the phosphorus content can be about 300 to about 1,500 milligrams per kilogram, specifically about 300 to about 1,300 milligrams per kilogram.

The solid substrate can have a low content of lignin. For example, the solid substrate can comprises less than or equal to 8 weight percent lignin, specifically less than or equal to 6 weight percent lignin, more specifically less than or equal to 2 weight percent lignin, on a dry weight basis.

The solid substrate includes enough water to support fungal growth. Typically, the solid substrate can be characterized as a moist solid, but not liquid. Thus, the ratio of water to solids will be such that the solid substrate retains the water therein without formation of a separate liquid phase. The precise ratio of water to solids will vary according to the composition of the solids and an optimum ratio can be determined without undue experimentation. In some embodiments, the solid substrate comprises about 100 to about 500 parts by weight water per 100 parts by weight total solids. Within this range, water amount can be about 200 to about 500 parts by weight, specifically about 300 to about 500 parts by weight.

In addition to the nutrients present in the insoluble solids of the solid substrate, additional nutrients can be added with the water used to form the solid substrate. For example, the solid substrate further can include about 1 to about 5 weight percent peptone, based on the total weight of the solid substrate. As demonstrated in the working examples below, it can be beneficial to first add the peptone at least one day after inoculation, rather than adding the peptone to the solid substrate before inoculation or simultaneously with inoculation. For example, the peptone can be added about 1 to about 14 days after inoculation, specifically about 2 to about 8 days after inoculation.

The depth of the solid substrate reflects a balance between encouraging growth of the fungal mass (which favors greater depths), facilitating recovery of fungal-derived products (which favors lesser depths), and mass transfer of air and water to maintain optimal growing conditions. Bed depths of about 1 to about 10 centimeters have been useful in achieving this balance. Within this range, the bed depth can be about 2 to about 8 centimeters, specifically about 2 to about 6 centimeters, more specifically about 2 to about 4 centimeters.

In addition to the step of forming a solid substrate, each of these embodiments above includes the step of inoculating the solid substrate with an inoculum comprising *Irpex lacteus*. *Irpex lacteus* is a resupinate polypore in the family Basidiomycota. The wild type fungus grows on dead hardwoods and is commonly found in North American and Europe. A wild type strain of *Irpex lacteus* is also commercially available as ATCC Number 20157. Another suitable strain of *Irpex lacteus* is designated ATCC Number 11245. While the working examples below demonstrate the efficacy of using wild type *Irpex lacteus*, it is also possible to use genetically engineered strains of *Irpex lacteus*. The inoculation step can occur before or after formation of the solid substrate. When the inoculation step occurs before the formation of the solid substrate, the substrate composition can be sterilized, then inoculated with a liquid or solid inoculant before being deposited on a platform to form the solid substrate. When the inoculation step occurs after the formation of the solid substrate, a liquid or solid inoculant can be added to the pre-formed substrate. There is no particular limitation on the form of the inoculant. Examples of suitable *Irpex lacteus* inoculants include portions of solid cultures on malt yeast agar and portions of liquid cultures in liquid malt yeast medium. In some embodiments, a liquid culture is processed in a high-speed blender or other high shear device to break up and distribute mycelium throughout the liquid inoculant.

After the solid substrate is inoculated with *Irpex lacteus*, the inoculated solid substrate is maintained under conditions sufficient to effect colonization of the solid substrate by an *Irpex lacteus* fungal mass. These conditions include a temperature of about 20 to about 40° C. and a pH of about 3 to about 7. Within the range of about 20 to about 40° C., the temperature can be about 25 to about 35° C., specifically about 25 to about 30° C. Within the range of about 3 to about 7, the pH can be about 4 to about 6, specifically about 4 to about 5. The time sufficient to effect colonization of the solid substrate by the *Irpex lacteus* is can be about 5 to about 27 days, specifically about 7 to about 25 days, more specifically about 7 to about 15 days. There is no particular limitation on the apparatus used for solid-state culturing of the inoculated substrate. Suitable apparatus are described, for example, in S. Tao, L. Zuohu, L. Deming, "A Novel Design of Solid State Fermenter and Its Evaluation for Cellulase Production by *Trichoderma veride* SL-1", *Biotechnology Techniques*, 1997, volume 10, pages 889-894; P. Cen, L. Xia, "Production of Cellulase by Solid-State Fermentation", *Advances in Biochemical Engineering/Biotechnology*, 1999, volume 65, pages 69-92; G. T. Tsao, C. S. Gon, N. J. Cao, "Repeated Solid-Phase Fermentation and Extraction for Enzyme Production", *Applied Biochemistry and Biotechnology*, 2000, volume 84-86, pages 505-524; and U.S. Pat. No. 6,197,573 B1 to Suryanarayan et al.

The culturing of *Irpex lacteus* is itself useful, given prior reports utilizing this fungus for purposes including the processing of dried beans to facilitate their rehydration (see, e.g., U.S. Pat. No. 4,333,955 of Murata et al), increasing the milk production of livestock (see, e.g., U.S. Pat. No. 4,144,354 of Unno et al.), and improving the flavor of dairy products (see, e.g., U.S. Pat. No. 3,858,492 of Mukai et al.). However, greater value can be derived from the *Irpex lacteus* fungal mass if its culture is used to produce cellulases, chitin, or both. Thus, in some embodiments, the method includes the step of extracting a cellulase from the colonized solid substrate. Extraction of cellulase—which can also be termed recovery of cellulase, given that the cellulase is an extracellular excretion of the fungus—can begin, for example, within about 3 to about 7 days of inoculation and continue through to the end of the culture period. Cellulase can be recovered by flushing the solid substrate with an aqueous fluid. The flushing can be conducted continuously or periodically. At the end of the last day of the culture period the colonized substrate can be macerated, optionally in the presence of a surfactant, to recover remaining cellulase. There is no particular limitation on the methods and apparatus used for cellulase recovery. Suitable methods and apparatus for recovery of extracellular enzymes in solid state fermentation of fungi are described, for example, in S. Tao, L. Zuohu, L. Deming, "A Novel Design of Solid State Fermenter and Its Evaluation for Cellulase Production by *Trichoderma veride* SL-1", *Biotechnology Techniques*, 1997, volume 10, pages 889-894; P. Cen, L. Xia, "Production of Cellulase by Solid-State Fermentation", *Advances in Biochemical Engineering/Biotechnology*, 1999, volume 65, pages 69-92; G. T. Tsao, C. S. Gon, N. J. Cao, "Repeated Solid-Phase Fermentation and Extraction for Enzyme Production", *Applied Biochemistry and Biotechnology*, 2000, volume 84-86, pages 505-524; and U.S. Pat. No. 6,197,573 B1 to Suryanarayan et al.

In some embodiments, the method includes the step of isolating chitin from the *Irpex lacteus* fungal mass. This step can be conducted with or without first separating the fungal mass from the remaining solid substrate. In either case, the fungal mass can be treated with a caustic solution of sodium hydroxide or the like to disperse the chitin-containing cell walls and hydrolyze the associated proteins. The resulting slurry can undergo filtration (e.g., a sequence of coarse filtration, microfiltration, and ultrafiltration) to separate the soluble protein hydrolyzates from the insoluble chitin. There is no particular limitation on the methods and apparatus used for chitin recovery. Suitable methods and apparatus for recovery of chitin from fungal biomass are described, for example, in U.S. Pat. No. 5,905,035 to Okada et al.; U.S. Pat. Nos. 6,255,085 and 6,399,338 and 6,485,946 to Chen et al.; P. Pochanavanich and W. Suntornsuk, "Fungal chitosan production and its characterization", *Letters in Applied Microbiology*, 2002, volume 35, 17-21; T. Wu, S. Zivanovic, F. Ann Draughon, C. E. Sams, "Chitin and Chitosan—Value Added Products from Mushroom Waste", *J. Agric. Food Chem.*, 2004, volume 52, pages 7905-7910; and T. C. Montenegro Stamford, T. L. Montenegro Stamford, N. P. Stamford, B. de Barros Neto, G. M. de Campos-Takaki, "Growth of *Cunninghamella elegans* UCT 542 and production of chitin and chitosan using yam bean medium", *Electronic Journal of Biotechnology*, 2007, volume 10, no. 1, pages 61-68. The recovered chitin can, optionally, be converted to chitosan using known techniques.

The invention is further illustrated by the following non-limiting examples.

EXAMPLES 1-8

Samples of *Irpex lacteus* were collected in the wild in Worcester County, Massachusetts, USA, and cultivated on malt yeast agar (MYA).

For Example 1, *Irpex lacteus* was cultivated in a glass Petri dish (100 millimeter internal diameter×25 millimeter depth) on a substrate consisting of water and a manufactured dried substrate precursor material with a high content of crystalline cellulose. An analysis of the dried substrate precursor material indicated that it contained 7,500 milligrams per kilogram of total nitrogen on a dry weight basis, and 1,200 milligrams per kilogram total phosphorus on a dry weight basis. Dispersing the dried substrate precursor material in water produced a pH of about 7. Water and dried substrate precursor material were mixed in a weight ratio of about 3:1. A ratio of less than 2:1 was insufficient to fully wet the dried substrate precursor material whereas a ratio of greater than 4:1 did not result in complete absorption of the water by the dried substrate precursor material. After the Petri dish with moist substrate was sterilized, the substrate was inoculated in the center of the dish with a 1 centimeter agar cube excised from a fresh solid MEA culture. The resulting inoculated substrate was cultured at 25° C.

For Examples 2-8, the procedure above was repeated except for variations in the inoculum source and the liquid mixed with dried substrate precursor material. In Table 1, "basal medium" contains 5 grams per liter ammonium tartrate, 1 gram per liter potassium phosphate ($KH_2PO_4$), 0.5 grams per liter magnesium sulfate heptahydrate ($MgSO_4.7H_2O$), 0.1 gram per liter yeast extract, and 0.001 gram per liter calcium chloride dihydrate ($CaCl_2.2H_2O$); "cellulose agar" contained 5 grams/liter ammonium tartrate, 1 gram/liter potassium dihydrogen phosphate ($KH_2PO_4$), 0.5 gram/liter magnesium sulfate heptahydrate ($MgSO_4.7H_2O$), 0.1 gram/liter yeast extract, 0.001 gram/liter calcium chloride dihydrate ($CaCl_2.2H_2O$), 0.4 weight/volume percent crystalline cellulose (Fluka Avicel PH-101), 1.6 weight/volume percent agar; "water with 10 g/L DMSA" refers to water with 10 grams/liter 2,2-dimethylsuccinic acid; "water with 20 g/L DMSA" refers to water with 20 grams/liter 2,2-dimethylsuccinic acid; "water with 40 g/L DMSA" refers to water with 40 grams/liter 2,2-dimethylsuccinic acid; and "water with 6 mL/L 35% HCl" refers to water with 6 milliliters per liter of 35% aqueous hydrochloric acid. Note that the use of 10, 20, and 40 grams per liter of 2,2-dimethylsuccinic acid were all insufficient to reduce the substrate pH to 4.5, whereas 6 milliliters per liter of 35% aqueous hydrochloric acid produced a substrate pH of about 4.5. Also in Table 1, "MEA solid culture" contains 20 grams/liter malt, 0.5 gram/liter yeast extract, and 20 grams/liter agar.

Figure 2:
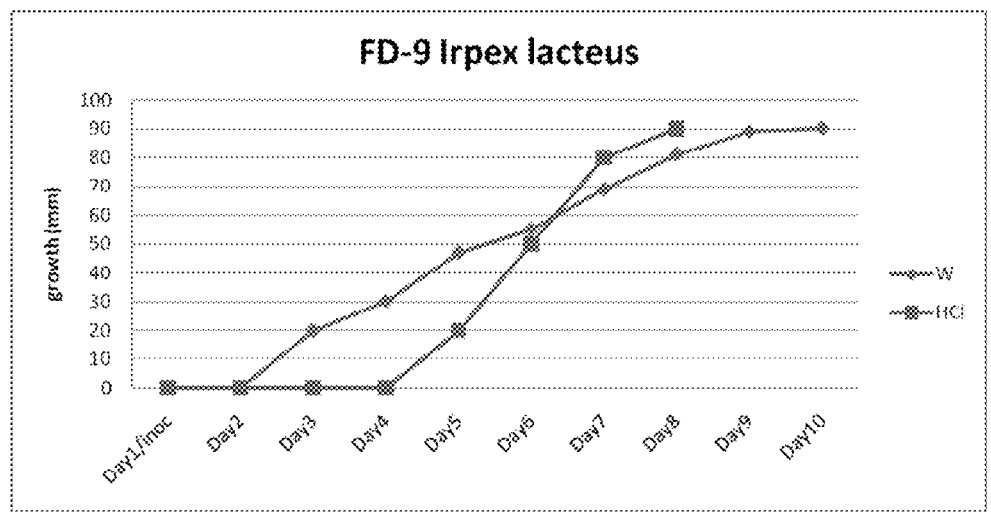
FIG. 2 is a plot of culture diameter versus time for solid substrates prepared with water (Example 1) and water acidified with milliliters per liter of 35% hydrochloric acid (Example 8).

For each example, the diameter of the culture was measured each day, and the day on which the surface of the substrate was covered with fungi was noted. The results presented in Table 1 show that the growth of *Irpex lacteus* was rapid and robust to variations in the inoculum source and the composition of the liquid used to prepare the substrate. The fastest growth occurred for samples 5-8, in which the liquid was acidified. FIG. 1 is a plot of culture diameter versus time for Example 1 (water) and Example 3 (basal medium). The results show, surprisingly, that growth was initiated and sustained more rapidly on a substrate prepared with water compared to a substrate prepared with basal medium. FIG. 2 is a plot of culture diameter versus time for Example 1 (water) and Example 8 (water with 6 mL/L 35% HCl). The results show that the initiation of growth was faster in water than aqueous HCl, but that the rate of growth was faster in aqueous HCl, with the net result that the fungus first covered the substrate prepared with aqueous HCl.

TABLE 1

| | Liquid | Inoculum | Days to Cover Substrate |
|---|---|---|---|
| Ex. 1 | water | MEA solid culture | 10 |
| Ex. 2 | water | cellulose agar solid culture | 10 |
| Ex. 3 | basal medium | MEA solid culture | 14 |
| Ex. 4 | basal medium | cellulose agar solid culture | 14 |
| Ex. 5 | water with 10 g/L DMSA | MEA solid culture | 9 |
| Ex. 6 | water with 20 g/L DMSA | MEA solid culture | 9 |
| Ex. 7 | water with 40 g/L DMSA | MEA solid culture | 9 |
| Ex. 8 | water with 6 mL/L 35% HCl | MEA solid culture | 8 |

EXAMPLES 9-11

These examples illustrate the effect of two different nitrogen sources, urea and peptone, on the growth of *Irpex lacteus*.

In these experiments, the dried substrate precursor material was physically agitated (processed in a Waring blending) before being mixed with water. The physical agitation had the effect of making the dried substrate precursor material absorbent. As a result, a 5:1 weight ratio of liquid to dried substrate precursor material was used to prepare the substrate.

For Example 9, the liquid used to prepare the substrate contained 1.25 weight percent urea; the weight ratio of liquid to dried substrate precursor material was 5:1; two duplicate samples were prepared, each in a 250 milliliter Erlenmeyer flask with 10 grams of dried substrate precursor material, 50 grams of liquid, and 3 milliliters of a liquid culture in malt yeast medium.

For Example 10, the Example 9 procedure was used except that the liquid used to prepare the substrate contained 1.25 weight percent peptone. For Example 11, the Example 9 procedure was used, except that water was used as the liquid used to prepare the substrate.

Fungal growth was monitored daily. Visual inspection of the cultures indicated that urea inhibits *Irpex lacteus* growth on this substrate. On the other hand peptone improved the rate of growth and the mycelial production of *Irpex lacteus*.

EXAMPLE 12

This example illustrates cellulase extraction from an *Irpex lacteus* culture.

Five identical samples of culture medium were each prepared by mixing in a 250 milliliter flask 100 milliliters of water containing 6 milliliters per liter of 35% hydrochloric acid, 1 weight percent peptone, and 0.1 volume percent of the nonionic surfactant polyoxyethylene (20) sorbitan monooleate (obtained as TWEEN 80); and 20 grams of physically agitated dried substrate precursor material. After sterilization, the culture medium was inoculated with 3 milliliters of a liquid culture in malt yeast medium.

On each of days 7, 12, 15, 20, and 25, a sample was divided into four equal parts, with each part being transferred to a 250 milliliter flask. To each flask was added 150 milliliters of water containing 0.1 volume percent TWEEN 80 surfactant and 0.91 weight/volume percent sodium chloride. The substrate was dispersed thoroughly into the liquid and then it was shaken for 90 minutes at 180 rpm and at 28° C. Then the mixture was filtered and the filtrate was kept on ice for protein determination. The filtrate was analyzed for cellulase activity using a modified protocol of B. Adney and J. Baker, "Measurement of Cellulase Activities", Aug. 12, 1996, available at http://www.nrel.gov/docs/gen/fy08/42628.pdf (last visited Nov. 2, 2009). A 0.5 milliliter portion (diluted to 1.5 milliliters) of the day 25 sample exhibited 0.57 milligram glucose release and 0.69 milligram glucose release per hour.

COMPARATIVE EXAMPLES 1-3

These examples illustrate attempts to culture *Irpex lacteus* on a substrate comprising amorphous cellulose.

For Comparative Example 1, 40 grams of amorphous cellulose were dispersed in water at a weight ratio of 1 part cellulose to 2 parts water, yielding a dispersion with a pH of about 6. After sterilization, the sample was inoculated with two 1-centimeter agar cubes from an active growing culture on MEA. Samples were cultured at 25° C. for 20 days.

For Comparative Examples 2 and 3, the procedure of Comparative Example 1 was followed, except that the weight ratios of cellulose to water were 1:2.5 and 1:3.

All samples exhibited weak growth, with microscopic examination revealing only some hyphae colonizing the substrate. These results, taken with the results above, illustrate the selectivity of *Irpex lacteus* to grow on crystalline cellulose rather than amorphous cellulose. This is surprising in that amorphous cellulose in generally recognized as easier to decompose by fungi than highly order crystalline cellulose. Moreover, the noted cellulase producers *Trichoderma reesei* RUT 30 (ATCC 56765), *Trichoderma reesei* QM 9414 (ATCC 26921), *Aspergillus niger* (ATCC 201202), and *Peni-*

*cillium pinophilum* (ATCC 200401), which are the parent sources of most of the industrial cellulase in use today, were all observed to be incapable of colonizing the crystalline cellulose substrate.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The invention claimed is:

1. A method of culturing the fungus *Irpex lacteus*, comprising:
    (a) forming a solid substrate comprising about 80 to about 98 weight percent cellulose on a dry weight basis; wherein the cellulose is about 55 to about 80 weight percent crystalline;
    (b) inoculating the solid substrate with an inoculum comprising *Irpex lacteus*; and
    (c) maintaining the inoculated solid substrate at a temperature of about 20 to about 40° C. and a pH of about 3 to about 7 for a time sufficient to effect colonization of the solid substrate by an *Irpex lacteus* fungal mass.

2. The method of claim 1, further comprising extracting a cellulase from the colonized solid substrate.

3. The method of claim 1, further comprising isolating chitin from the *Irpex lacteus* fungal mass.

4. The method of claim 3, further comprising converting the chitin to chitosan.

5. The method of claim 1, further comprising extracting a cellulase from the colonized solid substrate; and isolating chitin from the *Irpex lacteus* fungal mass.

6. The method of claim 1, wherein the solid substrate comprises about 44 to about 78 weight percent crystalline cellulose on a dry weight basis.

7. The method of claim 1, wherein the cellulose is alpha cellulose.

8. The method of claim 1, wherein the solid substrate comprises less than or equal to 8 weight percent lignin on a dry weight basis.

9. The method of claim 1, wherein the solid substrate has a thickness of about 1 to about 10 centimeters.

10. The method of claim 1, wherein the solid substrate comprises, on a dry weight basis, less than 5 weight percent of fibers having a thickness greater than or equal to 500 micrometers.

11. The method of claim 1, wherein the solid substrate comprises about 100 to about 500 parts by weight water per 100 parts by weight total solids.

12. The method of claim 1, wherein the *Irpex lacteus* is a wild type *Irpex lacteus*.

13. The method of claim 1, wherein the solid substrate is characterized by a total nitrogen content of about 1,000 to about 10,000 milligrams per kilogram on a dry weight basis.

14. The method of claim 1, wherein the solid substrate is characterized by an ammonia content of about 100 to about 1,000 milligrams per kilogram on a dry weight basis.

15. The method of claim 1, wherein the solid substrate is characterized by a phosphorus content of about 200 to about 2000 milligrams per kilogram on a dry weight basis.

16. The method of claim 1, wherein the solid substrate further comprises about 1 to about 5 weight percent peptone.

17. The method of claim 16, wherein the peptone is first added to the substrate at least one day after inoculation.

18. The method of claim 1, wherein the time sufficient to effect colonization of the solid substrate by the *Irpex lacteus* is about 5 to about 25 days.

* * * * *